(12) United States Patent
Ricco et al.

(10) Patent No.: US 6,730,206 B2
(45) Date of Patent: May 4, 2004

(54) MICROFLUIDIC DEVICE AND SYSTEM WITH IMPROVED SAMPLE HANDLING

(75) Inventors: Antonio J. Ricco, Los Gatos, CA (US); Travis D. Boone, San Mateo, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 280 days.

(21) Appl. No.: 09/810,895

(22) Filed: Mar. 17, 2001

(65) Prior Publication Data

US 2001/0030130 A1 Oct. 18, 2001

Related U.S. Application Data

(60) Provisional application No. 60/190,277, filed on Mar. 17, 2000, and provisional application No. 60/197,323, filed on Apr. 14, 2000.

(51) Int. Cl.[7] .............................................. G01N 27/453
(52) U.S. Cl. ........................ 204/604; 204/601; 422/100; 422/81
(58) Field of Search ................................. 204/451, 453, 204/601, 604; 422/100, 99, 68.1, 81

(56) References Cited

U.S. PATENT DOCUMENTS 5,858,187 A * 1/1999 Ramsey et al. ............. 204/452

* cited by examiner

Primary Examiner—Alex Noguerola
(74) Attorney, Agent, or Firm—Jacqueline F. Mahoney; Peter J. Dehlinger; Perkins Coie LLP

(57) ABSTRACT

An improved microfluidics device and system for sample loading and injection are disclosed. The device includes three main channels—a separation channel, supply channel, and drain channel—for use in loading and injecting a sample from the supply channel. Pairs of peripheral channels connecting the supply channel with upstream and downstream regions of the separation channel, and connecting supply and drain channels to a downstream region of the separation channel promote fluid flow and/or ion in the channel network to effect (i) sample shaping in the separation channel, when an electrokinetic or pneumatic force is applied between the supply and drain channels, and (ii) sample pullback in the supply and drain channels, when an electrokinetic or pneumatic force is applied between opposite ends of the separation channel. The system incorporates the device, electrodes that interact with reservoirs in the device, and a control unit.

11 Claims, 16 Drawing Sheets

MICROFLUIDIC DEVICE AND SYSTEM WITH IMPROVED SAMPLE HANDLING

This application claims the benefit of U.S. Provisional Application No. 60/190,277 filed Mar. 17, 2000 and U.S. Provisional Application No. 60/197,323 filed Apr. 14, 2000, both of which are incorporated herein by reference in their entirety.

FIELD OF THE INVENTION

The field of this invention is microfluidic devices and, in particular, a device designed for improved sample loading and injection.

BACKGROUND

Microtechnology has already and continues to revolutionize numerous aspects of performing operations. As part of this revolution, microfluidics offers small compact devices to perform chemical and physical operations with minute volumes. In this manner numerous events may be simultaneously performed within a small area using orders of magnitude less reagent and sample than possible with conventional 96-well plates. One aspect of microfluidics is the use of capillary electrokinesis to move materials in small volumes from one site to another on a solid substrate. Referred to commonly as $\mu$TAS or "lab-on-a-chip," these devices offer numerous advantages for performing chemical operations. The devices allow for mixing, carrying out chemical reactions, such as the polymerase chain reaction, genetic analysis, screening of physiological activity of drug candidates, and diagnostics, to mention only the more popular applications. The devices permit the use of much smaller amounts of reagents and sample, permit faster reactions, allow for easy transfer from one reaction vessel to another and separation of charged entities for rapid and accurate detection.

Numerous designs have been described in the literature for performing these operations in conjunction with particular protocols. Generally, one has a plurality of intersecting channels, particularly channels which join at an intersection. By applying appropriate voltage gradients, the volume in which the ions of interest reside can be relatively sharply delineated within a small volume, referred to as a plug. This operation is important in separations, when one wishes to have a high concentration of sample components to be detected in a sample plug, with little of the sample preceding or following the plug. There is interest in identifying different designs and protocols for carrying out plug formation followed by separation.

SUMMARY OF THE INVENTION

The invention includes, in one aspect, an improvement in a microfluidics device of the type having a supply channel for holding a sample, a drain channel, and a separation channel for containing an electrolyte buffer, where the supply and drain channels intersect said separation channel at a supply port and a drain port, respectively, and the ports define a sample-volume region in the separation channel between the two ports. The device further includes first, second, third, and fourth reservoirs communicating with the supply channel, the drain channel, and upstream and downstream ends of the separation channel, respectively, such that applying an electrokinetic or pneumatic force between the first and second reservoirs is effective to move a sample from the first reservoir through the sample-volume region in the separation channel and into the drain channel, and applying an electrokinetic or pneumatic force between the third and fourth reservoirs is effective to move a sample in the sample-volume region in the separation channel in a downstream direction.

The improvement, which is designed for improved sample handling, and in particular, improved sample loading and injecting, includes one or both of the following channel configurations, it being understood that in referring to sample streams, it may intend stream of solute ions as occurs in electrophoresis, liquid or ions as in electroosmosis, or streams of liquid containing dissolved or suspended species or particles, as in pneumatically driven liquid.

(a) First and second peripheral channels connecting the supply channel to upstream and downstream regions of the separation channel, respectively, on opposite sides of the sample-volume region. The two peripheral channels are dimensioned and configured such that applying an electrokinetic or pneumatic force between the first and second reservoirs is effective to move a sample from the first reservoir through the sample-volume region in the separation channel and into the drain channel, via the supply and drain channels, and to move electrolyte solution contained in the first and second peripheral channels and upstream and downstream regions of the separation channel toward the sample-volume region and into the drain channel, thereby shaping the sample in the sample-volume region during sample loading in a such manner that the leading and trailing edges of the sample plug are less diffuse, i.e., more sharply defined, than in the absence of such shaping flows; and (b) Second and third peripheral channels connecting the supply channel and the drain channel, respectively, to a downstream region of the separation channel, respectively. The two peripheral channels are dimensioned and configured such that applying an electrokinetic or pneumatic force between the third and fourth reservoirs is effective to move a sample in the sample-volume region in the separation channel in a downstream direction, and to move electrolyte solution contained in the upstream region of the separation channel through the second and third peripheral channels, a combination of flows known as "pull-back", thereby moving any components contained in the sample and drain channels away from the sample-volume region of the separation channel during sample injection, thereby maintaining or enhancing the lateral definition of the sample plug along its direction of motion.

In one general embodiment, the force applied between the reservoirs is an electrokinetic force produced by placing a voltage potential between the reservoirs.

In another general embodiment, the channel network includes both the first and second peripheral channels, for shaping sample in the sample-volume region during sample loading, and the third peripheral channel, for cooperating with the second channel during sample injection, to move sample contained in the sample and drain channels away from the sample-volume region of the of the separation channel. The device may include a fourth peripheral channel connecting the drain channel to an upstream portion of the separation channel.

The sample and drain ports may be axially aligned within the separation channel, whereby the sample-volume region includes the region of the separation channel between the two ports. Alternatively, the sample and drain ports may be axially offset along the separation channel, whereby the sample-volume region includes the region of the separation channel between the two ports, including the ports themselves.

In another embodiment, which includes the above first and second peripheral channels, the device further includes a second pair of peripheral channels, each of which extends from a first region along the sample channel, adjacent the first reservoir, and a second region along the sample channel adjacent the intersection of the sample channel with the separation channel. The second pair of peripheral channels are dimensioned and configured such that applying an electrokinetic or pneumatic force between the first and second reservoirs is effective to move a sample from the first reservoir through the sample channel toward the separation channel, and to move electrolyte solution contained in the second pair of peripheral channels from the first to the second regions in the sample channel, thereby shaping the sample in the sample channel as if is moved into the sample-volume-region of the separation channel.

In another aspect, the invention includes an improved microfluidics system that includes the microfluidics device above, electrodes adapted to contact liquid contained in the device reservoirs, and a control unit for control of the voltage potential difference between the first and second reservoirs, during sample loading, and between the third and fourth and reservoirs, during sample injection.

These and other objects and features of the invention will become more fully apparent when the following detailed description of the invention is read in conjunction with the accompanying drawings.

DETAILED DESCRIPTION OF THE INVENTION

Figure 1:
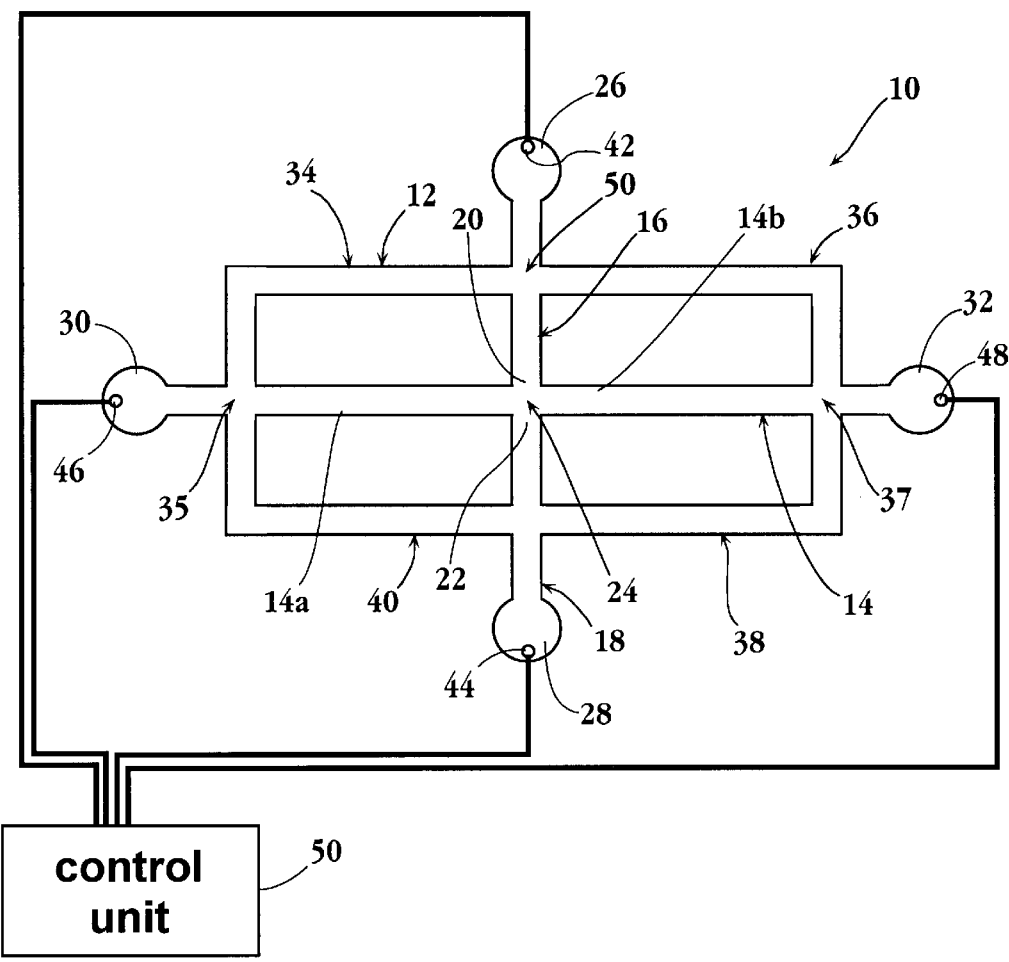
FIG. 1 shows in plan view, the channel geometry in one embodiment of the device of the invention.

An improved microfluidics device is provided for performing operations in a microfluidic device employing means for transporting bulk-phase fluid and/or ions, such as electrokinesis and pneumatics. The device has at least four reservoirs and may have more for particular purposes. Each of the four reservoirs is situated proximal to an end of a primary capillary channel, namely, one for sample delivery/shaping and the other for processing, such as injection and separation and detection.

In carrying out operations, one will frequently be interested in forming a sharply delineated small volume of one or more entities of interest (tight plug), where the entities are injected in a tightly compact or dense body or mass, with relatively sharply delineated borders for the entities in the liquid. Toward this purpose, the subject device uses two electrodes for performing the necessary operations for injecting a tight plug. The devices are so configured that by providing potential gradients using only two electrodes, the flow of ions and/or bulk-phase solution as a result of the resistances in the different channels results in the desired operations in the injection and processing of the sample ions.

The microfluidics device of the invention conventionally has three principal or main channels: (i) a supply channel for holding a sample, (ii) a drain channel, and (iii) a separation channel for containing an electrolyte buffer. The supply and drain channels intersect the separation channel at a supply port and a drain port, respectively, and the ports define a sample-volume region in the separation channel between the two ports.

The four reservoirs, designated first, second, third, and fourth reservoirs, are disposed at the free (distal) ends of the supply channel, the drain channel, and upstream and downstream ends of the separation channel, respectively. Conventionally, applying an electrokinetic or pneumatic force between the first and second reservoirs is effective to move a sample from the first reservoir through the supply channel, the sample-volume region in the separation channel and into the drain channel, and applying an electrokinetic or pneumatic force between the third and fourth reservoirs is effective to move a sample plug in the sample-volume region in the separation channel in a downstream direction.

The improvement of the device includes the addition of two or more peripheral channels connecting the supply channel with upstream and downstream portions of the separation channel, for purposes of controlling sample-plug volume, size, and shape during sample loading, and/or connecting the supply and drain channel to an upstream region of the separation channel, for producing pull back of sample into the supply and drain channels, during sample injection.

The device is formed on and contains a substrate or card in which the microstructures, primarily channels and reservoirs, are present and will generally have a thickness of at least about 20 $\mu$m, more usually at least about 40 $\mu$m, and not more than about 0.5 cm, usually not more than about 0.25 cm. The width of the substrate will be determined by the number of units to be accommodated and may be as small as about 2 mm and up to about 6 cm or more. The dimension in the other direction will generally be at least about 0.5 cm and not more than about 50 cm, usually not more than about 20 cm, and frequently not more than about 10 cm. An exemplary embodiment is roughly 8×12 cm, in conformity to the so-called "SSB Standard" dimensions of microtitre plates. The substrate may be a flexible film or relatively inflexible solid, where the microstructures, such as reservoirs and channels, may be provided by embossing, molding, machining, etc. The substrate may be of any convenient material, such as glass, plastic, silicon, fused silica, or the like, where depending on the nature of the operation, the channel surface may be coated to encourage or discourage or control the direction of electroendoosmosis.

The capillary channels may vary as to dimensions, width, depth and cross-section, as well as shape, being rounded, trapezoidal, rectangular, etc. The path of the channels may be straight, rounded, serpentine, meet at corners, cross-intersect, meet at tees, or the like. The channel dimensions will generally be in the range of about 0.1 $\mu$m to 1 mm deep and about 0.5 $\mu$m to 2 mm wide, where the cross-sectional area will generally be 0.1 $\mu m^2$ to about 0.25 $mm^2$. The channel lengths will vary widely depending on the operation for which the channel is to be used. The central separation channel will generally be in the range of about 0.05 mm to 50 cm, more usually in the range of about 0.5 mm to 10 cm, and in many cases not more than 5 cm, while the various portions of the channels other than the primary channels, the peripheral channels, will be within those ranges and frequently in the lower portion of the range.

The reservoirs will generally have volumes in the range of about 10 nl to 10 $\mu$l, usually having volumes in the range of about 20 nI to 1 $\mu$l. The reservoirs may be cylindrically shaped or conically shaped, particularly inverted cones, where the diameter of the open end or face of the reservoir will be from about 1.5 to 25 times, usually 1.5 to 15 times, the diameter of the bottom of the reservoir, where the reservoir connects to the channel.

In the discussion below, the peripheral channels will be referred to as (i) first peripheral channel, connecting the sample-supply channel to an upstream portion of the separation channel (upstream of the sample-volume region); (ii) second peripheral channel, connecting the sample-supply channel to a downstream portion of the separation channel; (iii) third peripheral channel, connecting the drain channel to a downstream portion of the separation channel; and (iv) fourth peripheral channel, connecting the drain channel to an upstream portion of separation channel.

The desired resistances in the main and peripheral channels can be achieved in a variety of ways, including length of the channel, cross-sectional area, obstructions narrowing the channel, non-conductive polymeric additives in the channel, and the like. For convenience, the channels may have different cross-sectional areas. In general, the flow of ionic species (measured as current) or bulk-phase liquid (measured as volume/unit time) is inversely proportional to the resistance to flow in the channel, where the resistance is proportional to the length of the channel and inversely proportional to the cross-sectional area of the channel. Thus, to reduce channel resistance, and thereby increase current flow in a given channel, one would increase the cross-sectional area of the channel and or decrease channel length.

Figure 6:
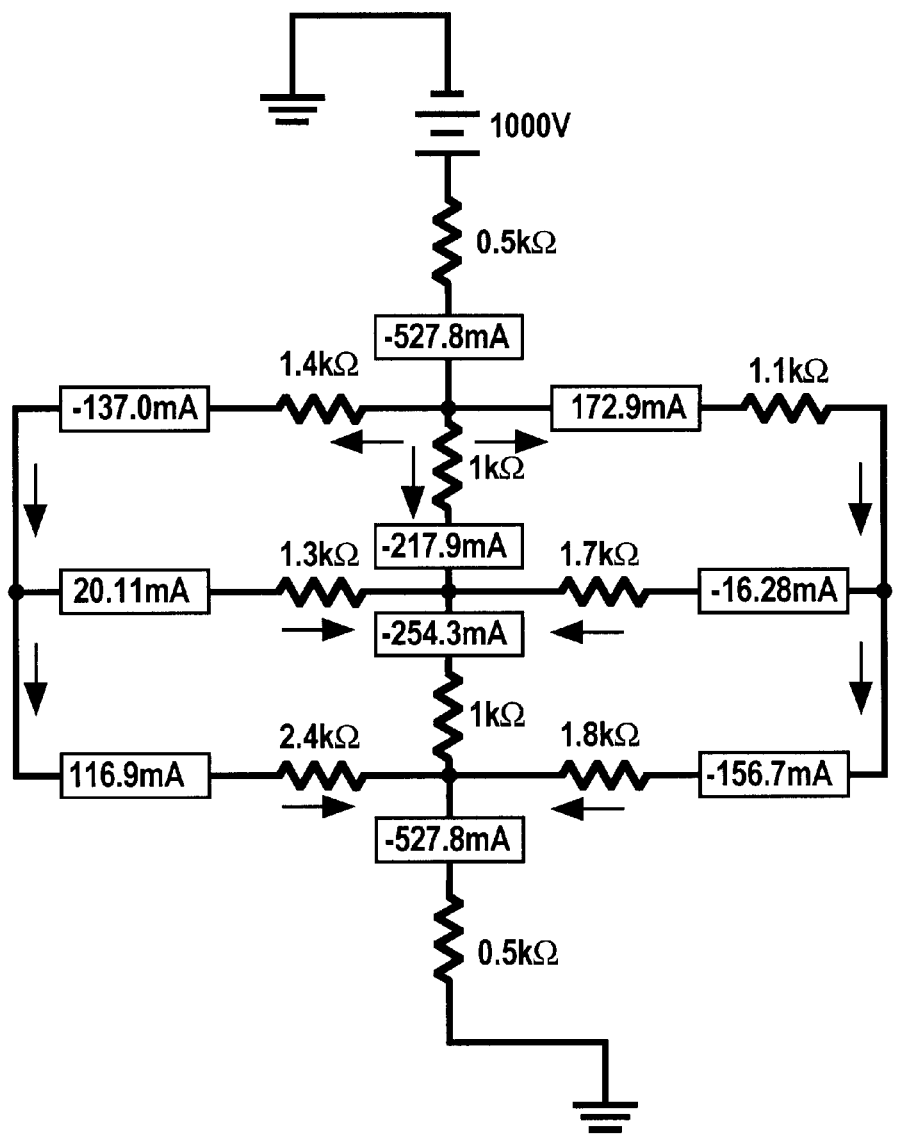
FIGS. 6 and 7 are electrical schematic diagrams providing illustrative channel resistances and current dispositions for performing loading and injecting separation operations as described for FIGS. 2 and 3, respectively.
Figure 11:
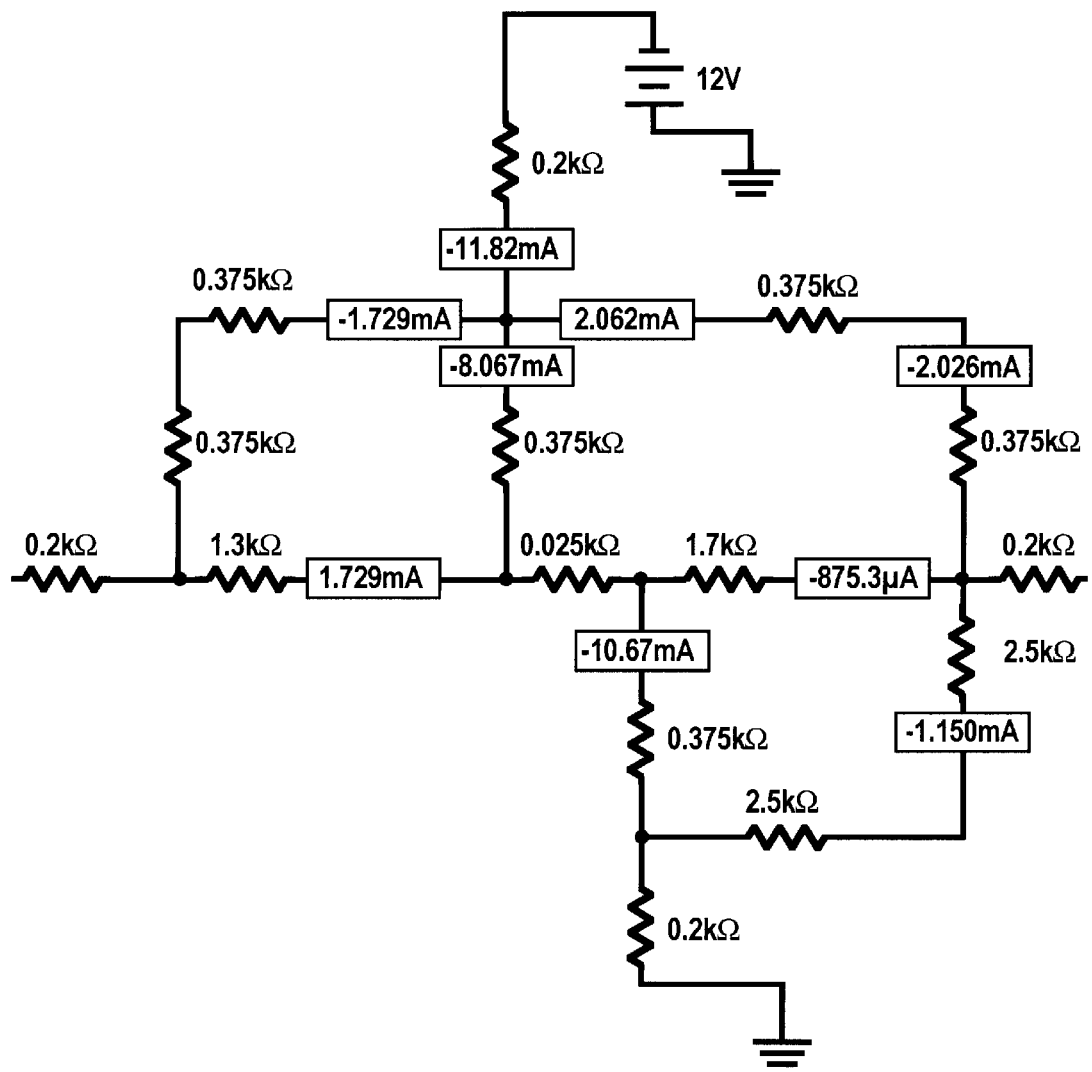
FIGS. 11 and 12 are electrical schematic diagrams providing illustrative channel resistances and current dispositions for performing injection and separation operations as described for FIGS. 8 and 9, respectively.
Figure 16:
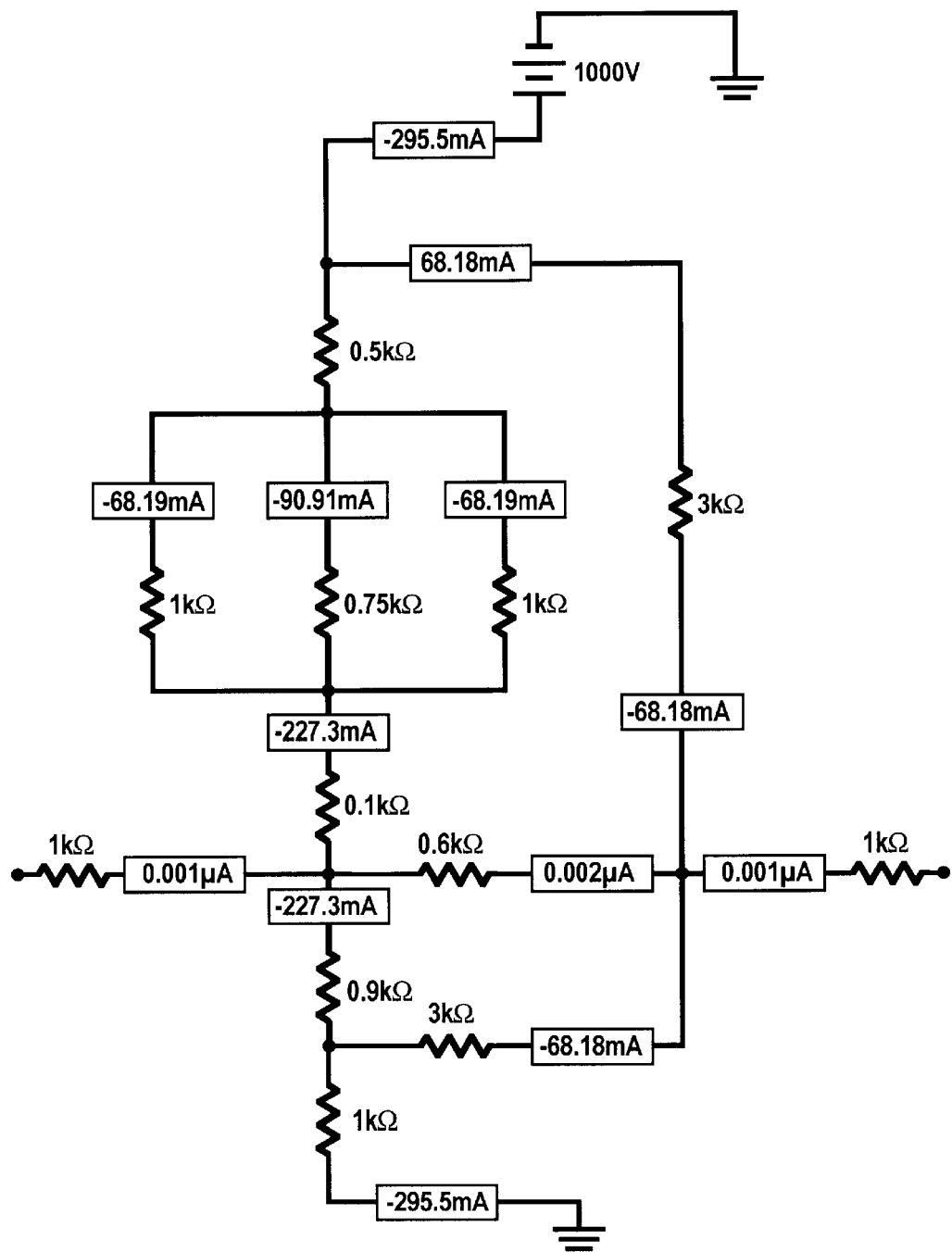
FIGS. 16 and 17 are electrical schematic diagrams providing illustrative channel resistances and current dispositions for performing the sample loading and injection operations described with respect to FIGS. 14 and 15, respectively.

Broadly considering the relative resistances/current flows required in sample loading, the first and second peripheral channels will function to move electrolyte solution in each peripheral channel toward the sample-volume region of the separation channel, to shape the sample material in the separation channel, as illustrated below in FIGS. 2, 9, and 14, for various embodiments of the invention. Commonly, the rate of electrolyte flow approaching the sample-volume region through the first peripheral channel will be on the order of 3–200% of the rate of flow of buffer and sample material moving directly between the sample and drain reservoirs; the rate of electrolyte flow approaching the sample-volume region through the second peripheral channel will be on the order of 1–25% of the rate of flow of buffer and sample material moving directly between the sample and drain reservoirs. Therefore, in general, the total lengths and cross-sectional areas of the first and second peripheral channels will be dimensioned and configured to provide the appropriate resistances relative to that of the supply and drain channels, such that the current flow in the two peripheral channels is preferably between about 3–200% in the first peripheral channel, and 1–25% in the second peripheral channel of the current flow directly between the sample and drain reservoirs. FIGS. 6, 11, and 16 discussed below illustrate exemplary resistance/current values in a device employing a voltage potential for sample loading.

Figure 7:
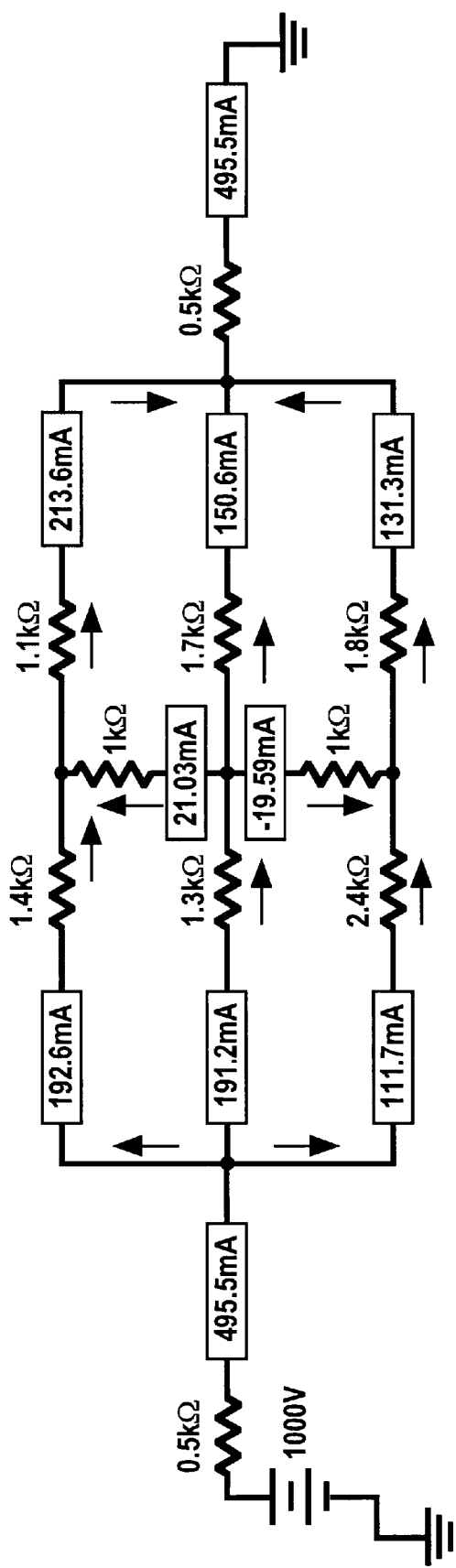
Figure 12:
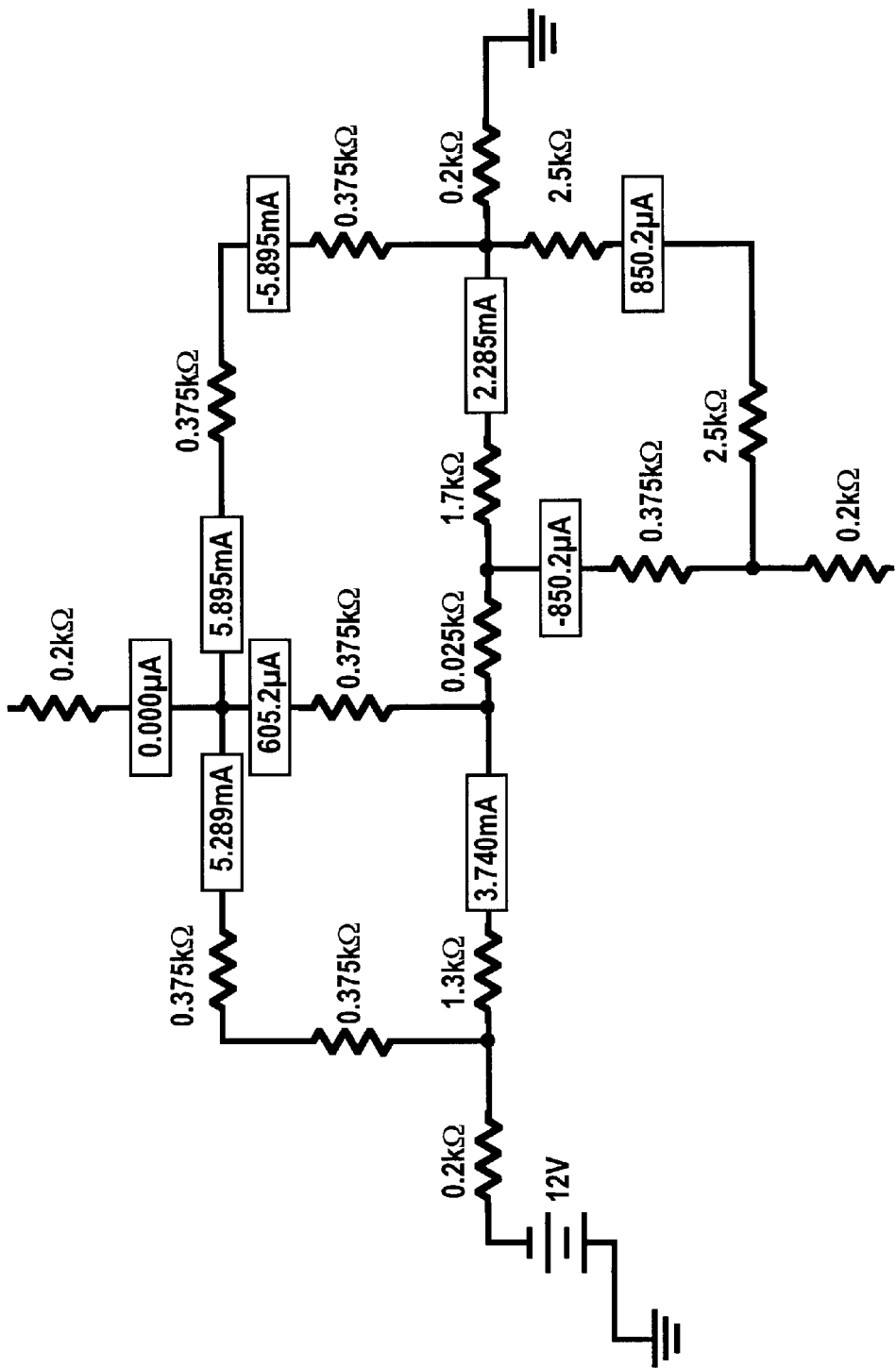
Figure 15:
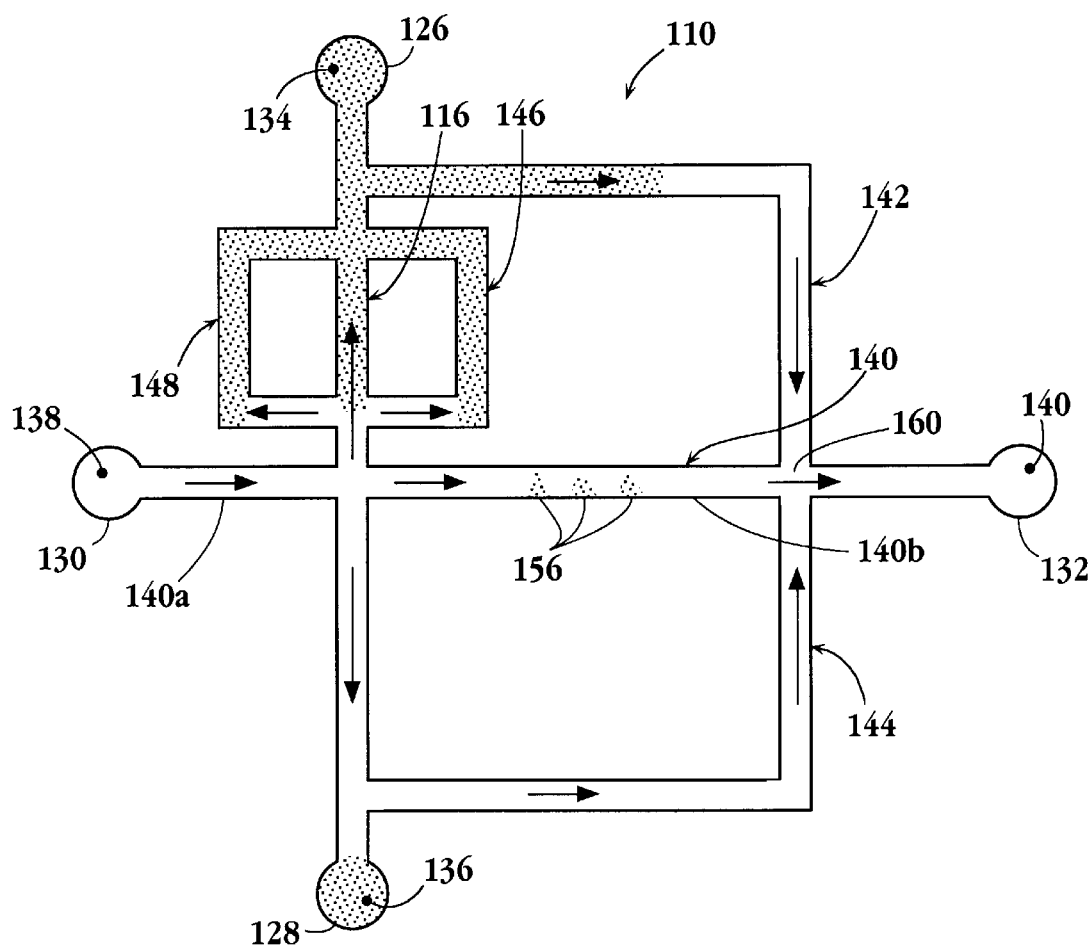
FIG. 15 is the same view of the device in FIG. 13, showing the injection of the plug with pull back and separation.

Considering the relative resistances/current flows required for sample pullback, the second and third peripheral channels will function to move electrolyte solution from the upstream portion of the separation channel into the supply and drain channels, as well as in a downstream direction in the separation channel, as illustrated below in FIGS. 3, 10, and 15, for various embodiments of the invention. The relative amount of electrolyte moving into each of the three channels will depend on the relative resistances of the second and third peripheral channels, and the downstream portion of the separation channel. Typically, it is desired to direct 10–110% or more of the quantity of flow entering the separation channel through the second peripheral channel, and to direct 20–150% of the quantity of flow entering the separation channel through the third peripheral channel for pullback during sample injection. This can be done, as above, by configuring and dimensioning the two peripheral channels to have the appropriate resistance relative to the other channels in the device. FIGS. 7, 12, and 15 discussed below illustrate exemplary resistance/current values in a device employing a voltage potential for sample injection.

The peripheral channels may engage the primary channels to form a cross-intersection or be offset so as to form tees. Usually the offset will be at least about 0.5 $\mu$m, more usually at least about 1.0 $\mu$m and not more than about 5 mm, usually not more than about 2 mm. The offset may serve to modify the resistances in the arms to enhance or restrict the movement of ions in one arm as compared to another, and the like.

Depending upon which layer serves as the channel layer, and the manner in which the channels are produced, e.g. embossed or molded, the enclosing surface will be below the channels to enclose them or above the channels to enclose them. When below, where for example the channels and reservoirs are molded into the substrate, an enclosing film or plate material may serve as a support for the device. Alternatively, the channels may be formed by embossing or molding, where the enclosing material is a cover. The substrate and/or the enclosing film may serve to form the reservoirs. The supporting film or plate material will generally be at least about 25 $\mu$m and not more than about 5 mm thick. The film or plate material used to enclose the channels and the bottom of the reservoirs will generally have a thickness in the range of about 10 $\mu$m to 2 mm, more usually in the range of about 20 $\mu$m to 1 mm. The selected thickness is primarily one of convenience and assurance of good sealing and the manner in which the devices will be used to accommodate instrumentation. Therefore, the ranges are not critical.

The area occupied by a single, comprised of the main channels, peripheral channels, and associated reservoirs, will vary widely, depending on the number of units of the device, the function of the units, and the like. As illustrative, for the most part, where the devices are designed to be compatible with 96 to 384 microtiter well plates, the units will have from about 4.5 to 9 mm spacings.

As indicated, the substrate may be a flexible film or inflexible solid, so the method of fabrication will vary with the nature of the substrate. For embossing, at least two films will be used, where the films may be drawn from rolls, one film embossed and the other film adhered to the embossed film to provide a physical support. The individual units may be scored, so as to be capable of being used separately, or the roll of devices retained intact. See, for example, application serial no. PCT/98/21869. Where the devices are fabricated individually, they will usually be molded, using conventional molding techniques. The substrates and accompanying film will generally be plastic, particularly organic polymers, where the polymers include addition polymers, such as acrylates, methacrylates, polyolefins, polystyrene, etc. or condensation polymers, such as polyethers, polyesters, e.g. polycarbonates, polyamides, polyimides, polysiloxanes, etc. Desirably, the polymers will have low fluorescence inherently or can be made so by additives or bleaching. The underlying enclosing film will then be adhered to a substrate by any convenient means, such as thermal bonding, adhesives, etc. The literature has many examples of adhering such films, see, for example, U.S. Pat. Nos. 4,558,333; and 5,500,071.

The subject devices find applications in many operations where a tightly defined plug of a single compound or a mixture is desired. These operations include genetic analysis, detection of single nucleotide polymorphisms, sequencing, haplotyping, enzyme assay analysis, candidate drug screening, proteomics, etc.

In a simple protocol, buffer is employed in the drain and two reservoirs at opposite ends of the separation channel, and sample is introduced into the remaining, supply reservoir. In carrying out the operation, a voltage gradient is applied between the supply and drain reservoirs, so that sample entities flow toward the intersection of the two channels with the separation channel. As the sample flows through the intersection, there is also flow from the arms of the peripheral channels, so as to produce a sample-shaping effect, as illustrated below with respect to FIGS. 2, 9, and 14. The electrodes in the remaining two reservoirs are allowed to float. The sample shaping is a result of the different resistances in the separation and peripheral channels, which affect the current and ion flow in the channels. The sample may be analyzed in the delivery channel or other operation performed.

In another embodiment, one may employ injection, pull back and separation. The process is initiated as described above. Once the shaped sample is formed, the voltages at the separation reservoirs are allowed to float and a voltage gradient established between the two reservoirs at the ends of the separation channel. By appropriate choice of resistances in peripheral channels and separation channel, upon injection, there will be concomitant pull back. During this period, the supply and drain reservoirs are allowed to float and the voltage gradient along the separation channel may be modified.

The timing of the operation and the dimensions of the channel arms are selected to inhibit the sample entities from extending from the peripheral channel arms into the separation channel. During the time prior to the injection, i.e., during sample loading, sample entities move from the sample reservoir down the delivery channel and into the arms of the peripheral channels. The injection is initiated prior to the sample entities arriving at the intersection of the delivery channel with the peripheral channels. The sample may then be transported through the separation channel for separation and detection or other processing.

For further understanding of the invention, the figures will now be considered. FIGS. 1–7 illustrate a first general embodiment having aligned supply and drain channels, and first, second, third, and fourth peripheral channels. A second general embodiment, having offset supply and drain channels, and first, second and third peripheral channels, is illustrated in FIGS. 8–12. A third general embodiment, illustrated in FIGS. 13–19, has aligned supply and drain channels, first and second peripheral channels, and additionally, a second pair of peripheral channels connecting upstream and downstream regions of the supply channel. It will be appreciated that the invention contemplates other embodiments consistent with the basic role of peripheral channel arms to create desired liquid-flow patterns in the channel network, including variations that combine feature of two or more of the embodiments described below.

Embodiment 1

In FIG. 1, the device 10 has a network 12 of channels, including a main separation channel 14, a supply channel 16, and a drain channel 18. The supply and drain channel intersect the separation channel at axially aligned ports 20, 22, respectively, forming between the two points a sample-volume region 24 in the separation channel. The sample volume region divides the separation channel into upstream and downstream segments 14a, 14b, respectively. As shown, channels 16 and 18 are terminated at their distal ends by first and second reservoirs 26, 28, respectively, and the upstream and downstream ends of the separation channel are terminated at their ends by third and fourth reservoirs 30, 32 respectively. Also shown are: a first peripheral channel 34 connecting the supply channel to an upstream region 35 of the separation channel; a second peripheral channel 36 connecting the supply channel to a downstream region 37 of the separation channel; a third peripheral channel 38 connecting the drain channel to downstream region 37 of the separation channel; and a fourth channel 40 connecting the drain channel to upstream region 35 of the separation channel. Also shown are electrodes 42, 44, 46, 48 that are placed or adapted to be placed in reservoirs 26, 28, 30, and 32, respectively. The electrodes are connected to a voltage control unit 50 that operates to control the voltage to the electrodes for sample loading, sample injection, and sample separation, as will be described below.

Where the device is designed for fluid movement by a pneumatic force, the reservoirs in the device are operatively connected to a suitable pneumatic source, such as a source of compressed sample or electrolyte buffer, for producing a liquid pressure differential between selected reservoirs.

Figure 2:
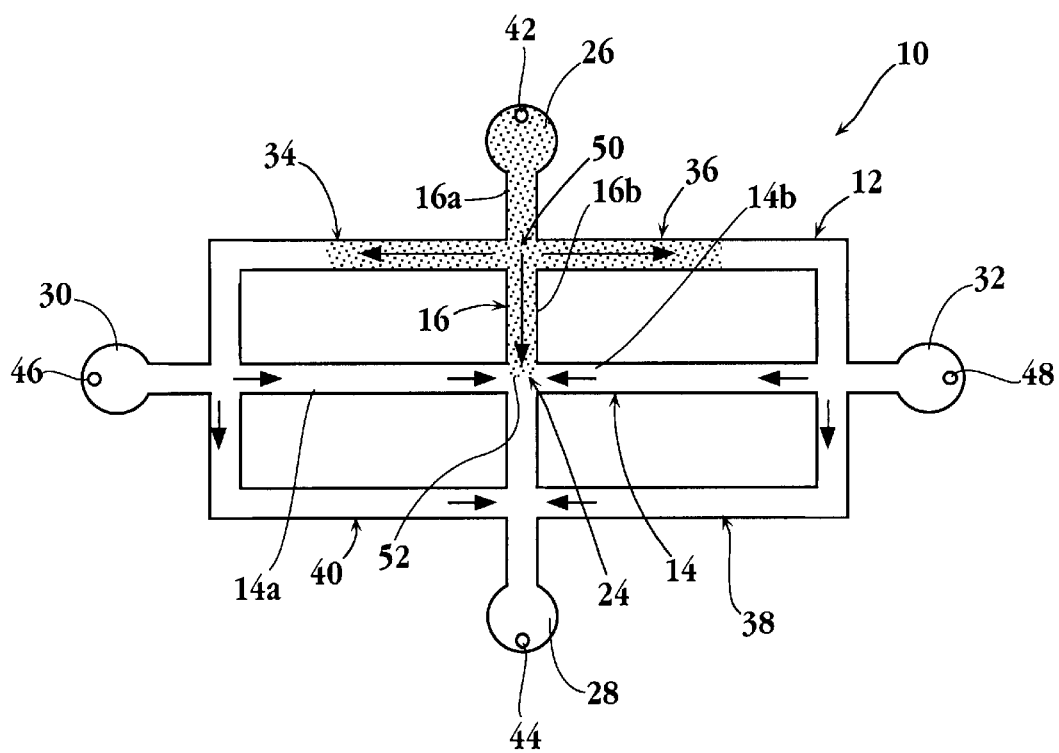
FIG. 2 is the same view of the device in FIG. 1, showing the formation of a plug with shaping at the intersection.

In FIG. 2, the device is shown in operation; the numbering convention is the same as that used in FIG. 1. The operation is to deliver a sample stream from the sample reservoir, through the supply channel, to the sample-volume region, where it is electrokinetically "shaped" in preparation for subsequent electrokinetic injection and separation. The operation is performed by first introducing an electrolyte buffer solution into the device 10, so that the channels are filled and electrolyte is present in the reservoirs. Sample may then be added to reservoir 26, so that the solution in reservoir 26 is different from the solution in the remainder of the device 10. Electrodes 42, 44 in reservoirs 26, 28, respectively, are activated to provide a potential gradient between the two reservoirs to induce electrokinetic flow through the system from reservoir 26 toward reservoir 28, e.g., electroosmotic bulk-phase flow and/or electrophoretic solute-ion flow. At intersection 50, where the supply channel communicates with the first and second peripheral channels, sample ion flow from supply channel segment 16a is split into three streams down channels 34, 36, and 16. During this process, electrodes 46 and 48 in reservoirs 30, 32 are allowed to float. The result of the electrokinetic splitting of the flow from the sample reservoir 26 at intersection 50 and convergence of the liquids at sample-volume region 24 is the formation of a shaped sample stream or plug 52 in sample-volume region 24, with the sample ion flow sandwiched between flow of the buffer ions from upstream and downstream sides of the separation channel, all moving toward reservoir 44.

Arrows in FIG. 2 show the direction of flow at various locations in the network of channels for this operation. The sample stream may be analyzed while in any of the segments of channel 14 or the pinched sample stream 52 may be used for injection and further processing as shown in FIG. 3.

Note that the potential motivating flow in this operation could similarly be achieved via pneumatics (pressure/vacuum), instead of voltage, to deliver and pinch sample at intersection 24. For example, pressure would be applied to reservoir 26, while applying vacuum at reservoir 28. The exposure of reservoirs 30, 32 to atmospheric pressure (or an applied pressure less than that on reservoir 26) would be analogous to electrically floating those reservoirs.

Figure 3:
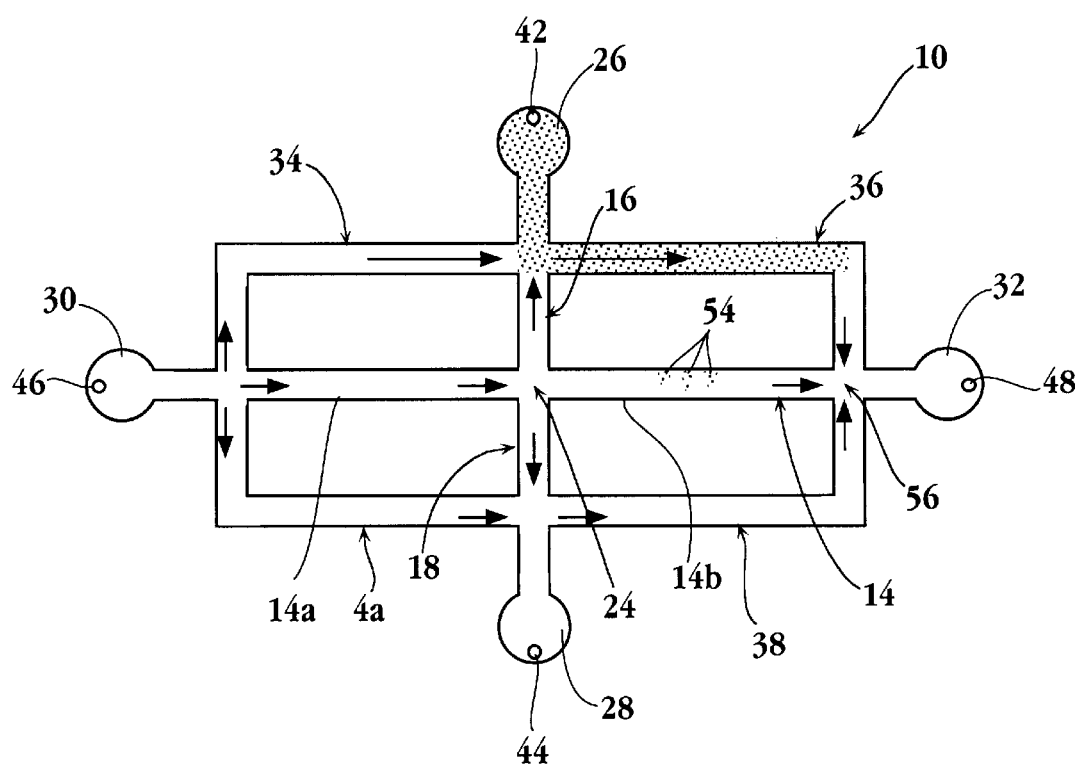
FIG. 3 is the same view of the device in FIG. 1, showing the injection of the plug with pull back and separation.

The numbering for FIG. 3 will be same as the numbering used for FIGS. 1 and 2. In FIG. 3, the device 10 is shown at the stage where the sample ions and/or bulk-phase sample volume have been electrokinetically injected from the shaped stream 52 (see FIG. 2) at intersection 24 into separation channel segment 14b. In this operation, electrodes 42, 44 are allowed to float, and electrodes 46, 48 are activated to provide a voltage gradient between reservoirs 30, 32, producing electrokinetic flow through the system from sample-volume region 24 toward reservoir 32. In particular, the voltage gradient between electrodes 46, 48 directs the shaped sample 52 (see FIG. 2) into channel segment 14b. At the same time, buffer ion flow in channel segment 14a moves into channels 16, 18, so as to displace sample species in those delivery channel segments. This is referred to as "pull back" and serves to prevent leakage of sample species from channels 16, 18 into the separation channel, which would interfere with the analysis of the sample species. The pull back is achieved due to the relative resistance of loops containing the second and third peripheral channels relative to that of the separation channel segment 14b, as discussed above.

Arrows in FIG. 3 show the direction of flow at various locations in the network of channels for this operation. Depending on the nature of the medium in separation channel segment 14b, and the nature of the sample ions, the shaped sample 52 (see FIG. 2) may be subjected to electrophoretic separation into fractions 54, based on the mobility of the fractions in the medium in 14b. Detection is performed prior to the sample fractions reaching intersection 56, where ion streams from channels 36, 38 converge on their way to reservoir 32. The subject device using control of only two electrodes at any one time provides for accurate movement of sample ions, shaping and analysis, simplifying the control system and ostensibly reducing the cost and complexity of the power supply required driving such a system.

Figure 4:
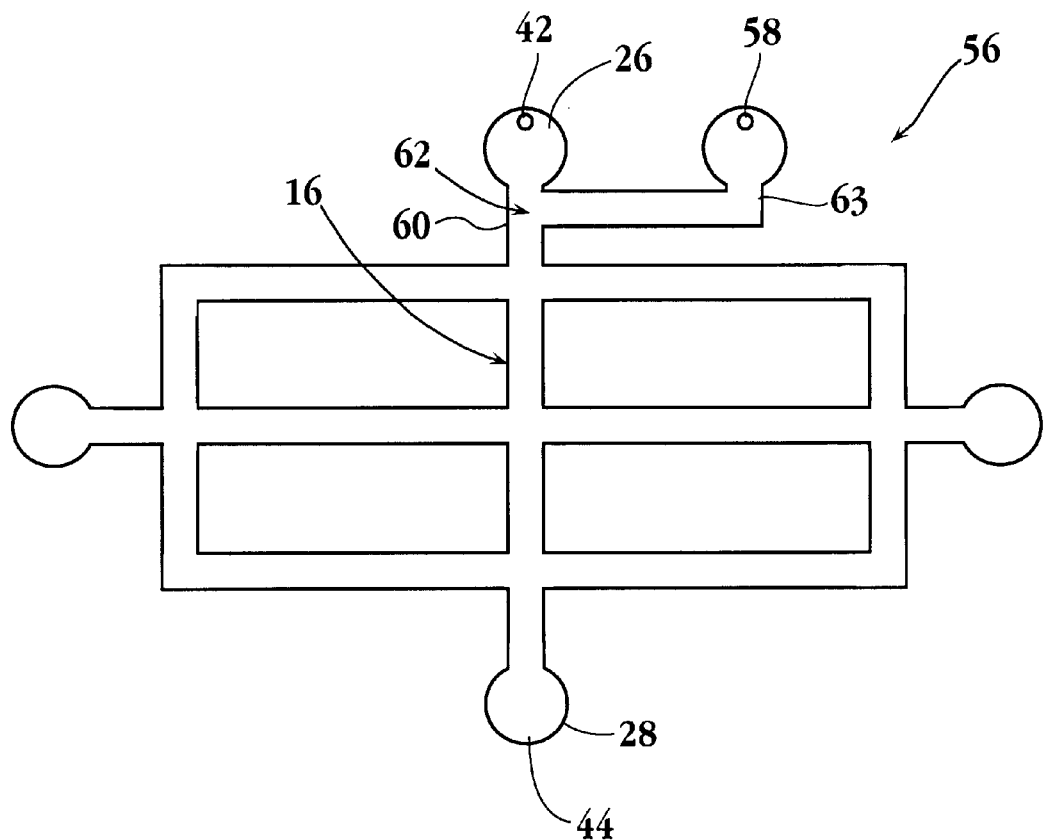
FIG. 4 is a plan view like that in FIG. 1, but showing an alternative embodiment of the device.

To provide further versatility, in FIG. 4, a similar device 56, which has substantially the same configuration as the device of FIG. 1, has an additional reservoir 58 connected to delivery channel arm 60 through a connecting channel 63. Otherwise, all of the other structures are as identified in FIGS. 1–3. Reservoir 58 would contain buffer, which buffer would serve to purge the channel network of sample after each operation. A potential gradient applied between reservoirs 58 at one voltage potential, and reservoirs 26 and 28 at other voltages, by applying a voltage to electrodes 58, 42, and 44, draws buffer (or other cleaning reagent) from reservoir 58 into intersection 62 where it will bifurcate in supply channel 16, flowing toward reservoirs 26 and 28. Note that the potential gradient to motivate flow could also be created pneumatically by applying a higher pressure to reservoir 58 and lower pressures (or vacuum) to reservoirs 26, 44. In this manner, the system may be purged of sample ions between subsequent injection runs. If desired, the initial sample could then be removed from reservoir 26 and replaced with a different sample for a subsequent run.

Figure 5:
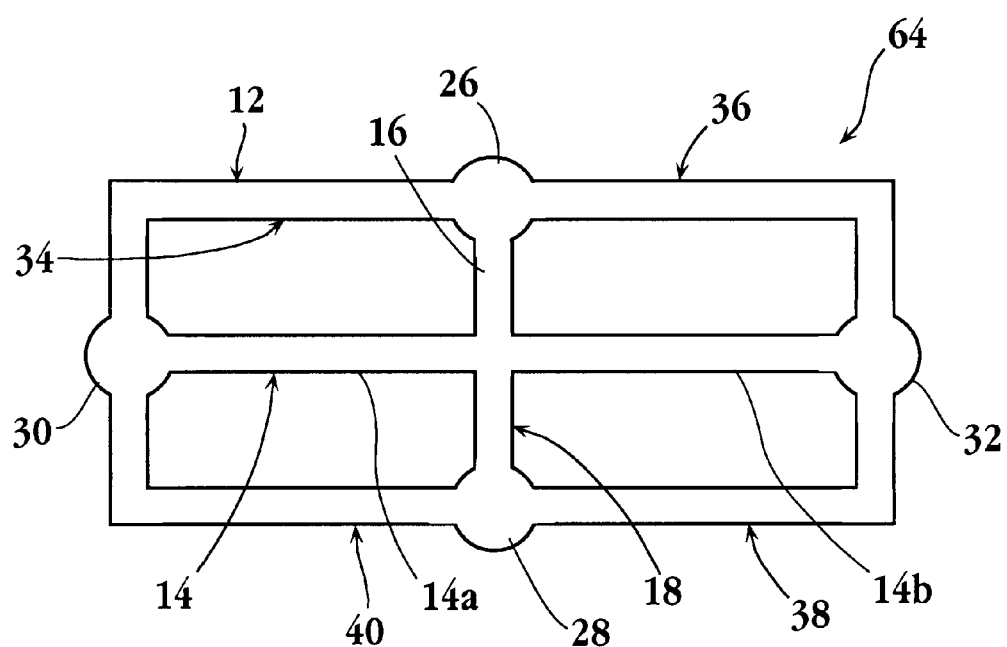
FIG. 5 is a plan view like that in FIG. 1, but showing a further alternative embodiment of the device.

In FIG. 5 an alternative embodiment of a device 64 is depicted, where the common features will have the same designation as FIGS. 1–3. The device has a network of channels comprising supply and drain channels 16, 18, respectively, separation channel 14, peripheral channels 34, 36, 38, and 40, and reservoirs 26, 28, 30, and 32. The device differs from device 10 in that the reservoirs are formed at the intersection of three channels, including the peripheral channels, rather than at the extending ends of the main channels. Thus, each reservoir serves as a 3-way intersection. This configuration reduces the risk of current-generated Joule heating within channels by eliminating segments which would carry the greatest current, namely the channel entrances to reservoirs. This configuration further simplifies the process of filling the initially dry (empty) device channels with buffer solution, as there is less opportunity for the trapping of air bubbles during such filling process.

FIGS. 6 and 7 are electrical diagrams indicating exemplary resistances, applied voltages, and resulting currents in the device for performing sample delivery/pinch and injection/separation, respectively. It is to be understood that scaling applies, so that, for example, kΩ may be increased to MΩ and mA would be concurrently reduced to $\mu$A. The diagrams conform to what is happening in FIGS. 2 and 3, respectively. The combinations of channel resistances and applied voltages can be altered to achieve other desired currents in each segment of the channel network.

Embodiment 2

Figure 8:
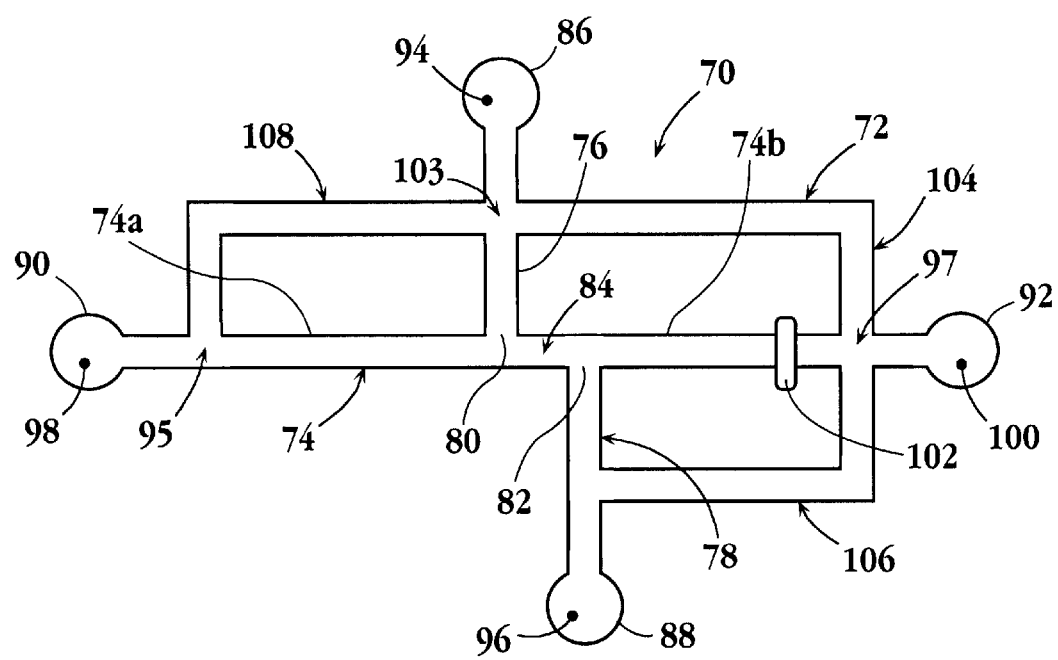
FIG. 8 shows in plan view, the channel geometry in a second general embodiment of the device of the invention.
Figure 9:
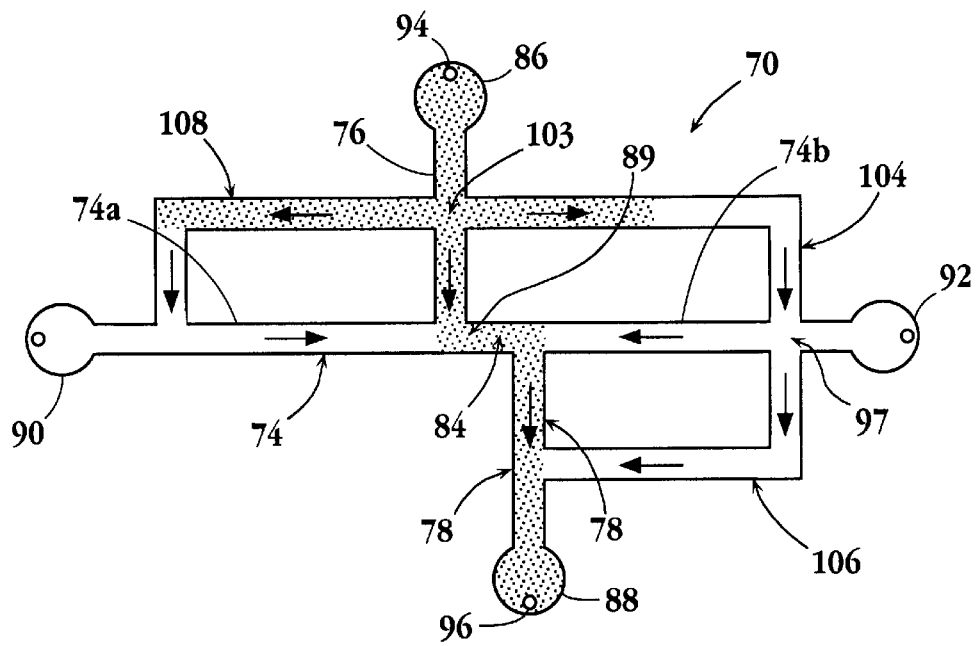
FIG. 9 is the same view of the device in FIG. 8, showing the formation of a sample plug with shaping at the intersection.
Figure 10:
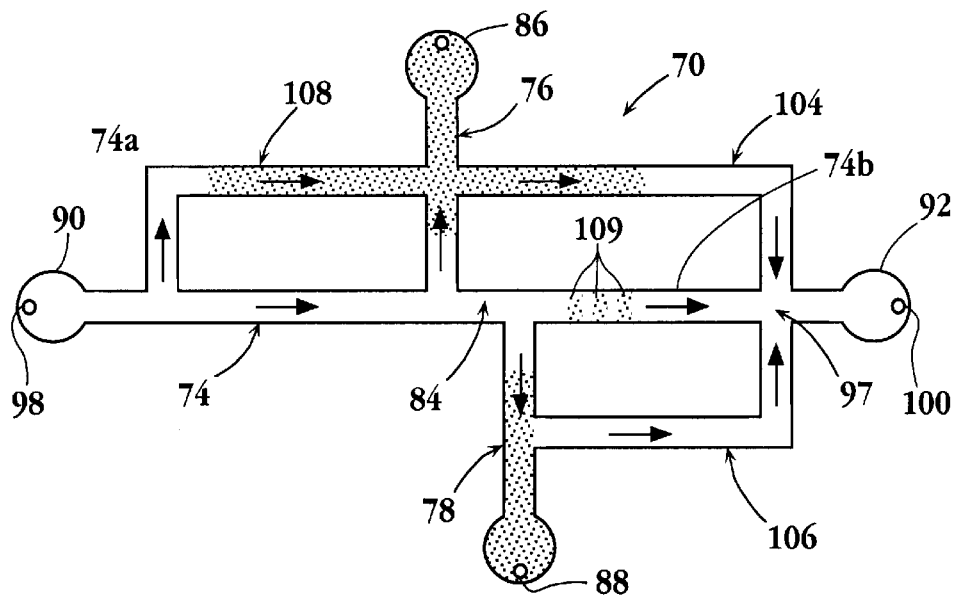
FIG. 10 is the same view of the device in FIG. 8, showing the injection of the plug with pull back and separation.

According to a second embodiment of the invention, illustrated in FIGS. 8–10, a device 70 has a network 72 of channels, including a main separation channel 74, a supply channel 76, and a drain channel 78. The supply and drain channel intersect the separation channel at axially aligned ports 80, 82, respectively, forming between the two points a sample-volume region 84 that extends from the upstream side of port 80 to the downstream side of port 82. As above, the sample volume region divides the separation channel into upstream and downstream segments 74a, 74b, respectively. Also as above, channels 76 and 78 are terminated at their distal ends by first and second reservoirs 86, 88, respectively, and the upstream and downstream ends of the separation channel are terminated at their ends by third and fourth reservoirs 90, 92 respectively. Also shown are: a first peripheral channel 108 connecting the supply channel to an upstream region 95 of the separation channel; a second peripheral channel 104 connecting the supply channel to a downstream region 97 of the separation channel; and a third peripheral channel 106 connecting the drain channel to downstream region 97 of the separation channel. Also shown are electrodes 94, 96, 98, 100 placed or adapted to be placed in reservoirs 86, 88, 90, and 92, respectively. The electrodes are connected to a voltage control unit (not shown) that operates to control the voltage to the electrodes for sample loading, sample injection, and sample separation, as will be described below.

Where the device is designed for fluid movement by a pneumatic force, the reservoirs in the device are operatively connected to a suitable pneumatic source, such as a source of compressed sample or electrolyte buffer, for producing a liquid pressure differential between selected reservoirs.

FIG. 9 illustrates the operation of the device during sample loading, where sample from the sample reservoir is moved through the supply channel, and into and through the sample-volume region, where it is electrokinetically "shaped" or "confined" in the sample-volume region for subsequent electrokinetic injection and separation. The operation is performed by first introducing an electrolyte buffer solution into the device 70, and a sample into reservoir 86, as described with reference to FIG. 2. Electrodes 92, 96 are activated to provide a potential gradient between the two reservoirs to induce electrokinetic flow through the system from reservoir 86, through the supply channel, into and through sample-volume region 84, and toward reservoir 88 via the drain channel.

At intersection 103 in the supply channel, where the supply channel communicates with the first and second peripheral channels, sample ion flow from supply channel segment is split into three streams along channels 76, 104, and 108. During this process, electrodes 98, 100 in reservoirs 90, 92 are allowed to float. The result of the electrokinetic splitting of the flow from the sample reservoir 86 at intersection 103 and convergence of the liquids at sample-volume region is that (i) on the upstream side, electrolyte solution flowing through channel 108 and segment 74a flows against and under the upstream side of the sample in the separation channel, toward drain channel 78, acting to confine and shape the sample at its upstream side, and (ii) on the downstream side, electrolyte solution flowing through channel 104 and segment 74b flows against the downstream side of the sample in the separation channel, also into drain channel 78, acting to confine and shape the sample at its downstream side. The result is a confined sample volume 89 in the sample-volume region. The arrows in FIG. 8 show the direction of flow at various locations in the network of channels for this operation.

As in the first embodiment of the device, the potential motivating flow in this operation could similarly be achieved via pneumatics (pressure/vacuum), instead of voltage, to deliver and pinch sample at sample-volume region 84.

In FIG. 10, the device is shown at the stage where the sample ions and/or or bulk-phase sample volume have been electrokinetically injected from the confined sample volume 89 (see FIG. 2) in region 84 into separation channel segment 74b. In this operation, electrodes 86, 88 are deactivated and allowed to float. The electrodes 90 and 92 are activated to provide a voltage gradient between reservoirs 90, 92, producing electrokinetic flow through the system from sample-volume region 84 toward reservoir 92. At the same time, buffer ion or bulk-phase electrolyte flow from channel segment 74a moves into channels 76, 78 so as to displace sample in those channels. As above, this pullback effect serves to prevent leakage of sample species from channels 76, 78 into the separation channel, which would interfere with the analysis of the sample species. The pull back is achieved due to the relative resistance of loops containing the second and third peripheral channels relative to that of the separation channel segment 74b, as discussed above.

Arrows in FIG. 10 show the direction of flow at various locations in the network of channels for this operation. Depending on the nature of the medium in separation channel segment 74b, and the nature of the sample ions, the shaped sample 89 may be subjected to electrophoretic separation into fractions 109, based on the mobility of the fractions in the medium in 74b. Detection (at detector, 102 in FIG. 8) is performed prior to the sample fractions reaching intersection 97, where ion streams from channels 104, 106 converge on their way to reservoir 92. As above. This embodiment requires control of only two electrodes at any one time, while providing for accurate movement of sample ions or bulk-phase sample material, shaping and analysis, simplifying the control system and ostensibly reducing the cost and complexity of the power supply required driving such a system.

FIGS. 11 and 12 are electrical diagrams indicating exemplary resistances, applied voltages, and resulting currents in the device for performing sample delivery/pinch and injection/separation, respectively, where the above scaling feature applies. The diagrams conform to what is happening in FIGS. 9 and 10,, respectively. The combinations of channel resistances and applied voltages can be altered to achieve other desired currents in each segment of the channel network.

Embodiment 3

Figure 13:
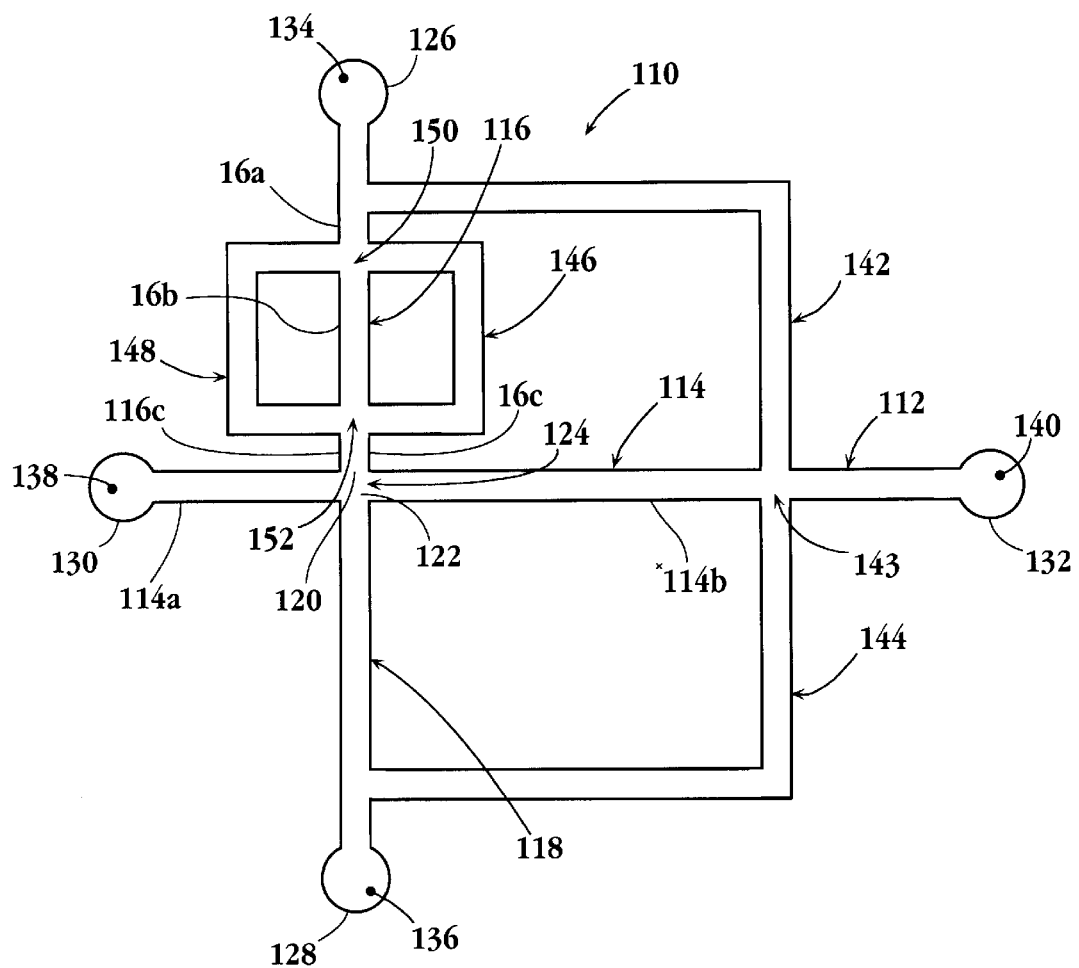
FIG. 13 shows in plan view, the channel geometry in a third general embodiment of the device of the invention.

FIG. 13 shows a plan view of a device 110 constructed in accordance with a third embodiment of the invention. Similar to device 10 described above, the device has a network 112 of channels, including a main separation channel 114, a supply channel 116, and a drain channel 118. The supply and drain channel intersect the separation channel at axially aligned ports 120, 122, respectively, forming between the two points a sample-volume region 124 in the separation channel. The sample volume region divides the separation channel into upstream and downstream segments 114a, 114b, respectively. As shown, channels 116 and 118 are terminated at their distal ends by first and second reservoirs 126, 128, respectively, and the upstream and downstream ends of the separation channel are terminated at their ends by third and fourth reservoirs 130, 132 respectively. Also shown are a first peripheral channel 142 connecting the supply channel to a downstream region 143 of the separation channel and a second peripheral channel 144 connecting the drain channel to downstream region 143 of the separation channel. Also shown are electrodes 134, 136, 138, and 140 that are placed or adapted to be placed in reservoirs 126, 128, 130, and 132, respectively. The electrodes are connected to a voltage control unit (not shown), as in device 10, that operates to control the voltage to the electrodes for sample loading, sample injection, and sample separation, as will be described below. Alternatively, where the device is designed for fluid movement by a pneumatic force, the reservoirs in the device are operatively connected to a suitable pneumatic source, such as a source of compressed sample or electrolyte buffer, for producing a liquid pressure differential between selected reservoirs.

To obtain a shaping of the sample stream just upstream of intersection 124, a pair of peripheral channels 146, 148 are joined to supply channel 116 at intersections 150, 152. In general, intersections 124, 152 will be separated by a small channel that will have very low resistance, generally being a distance which may be as small as permitted by the fabrication process and not more than about 10% of the length of the supply channel 116, usually not more than about 5%, and may be as small as about 0.01 mm, usually not less than about 0.1 mm. The time for an entity to move down channel segment 116 from intersection 150 to 152 will be significantly less through section 136 than through the two peripheral channels 146, 148. Therefore, sample entities flowing through the two channels, 146, 148 will not meet with the sample entities flowing through the supply channel section 116 during the course of the operation.

In carrying out the delivery process, the channels will usually be filled with an appropriate buffer, so that the channels will be filled and there will be ample liquid in the reservoirs. At the appropriate time, sample may be introduced into reservoir 126 for processing.

Figure 14:
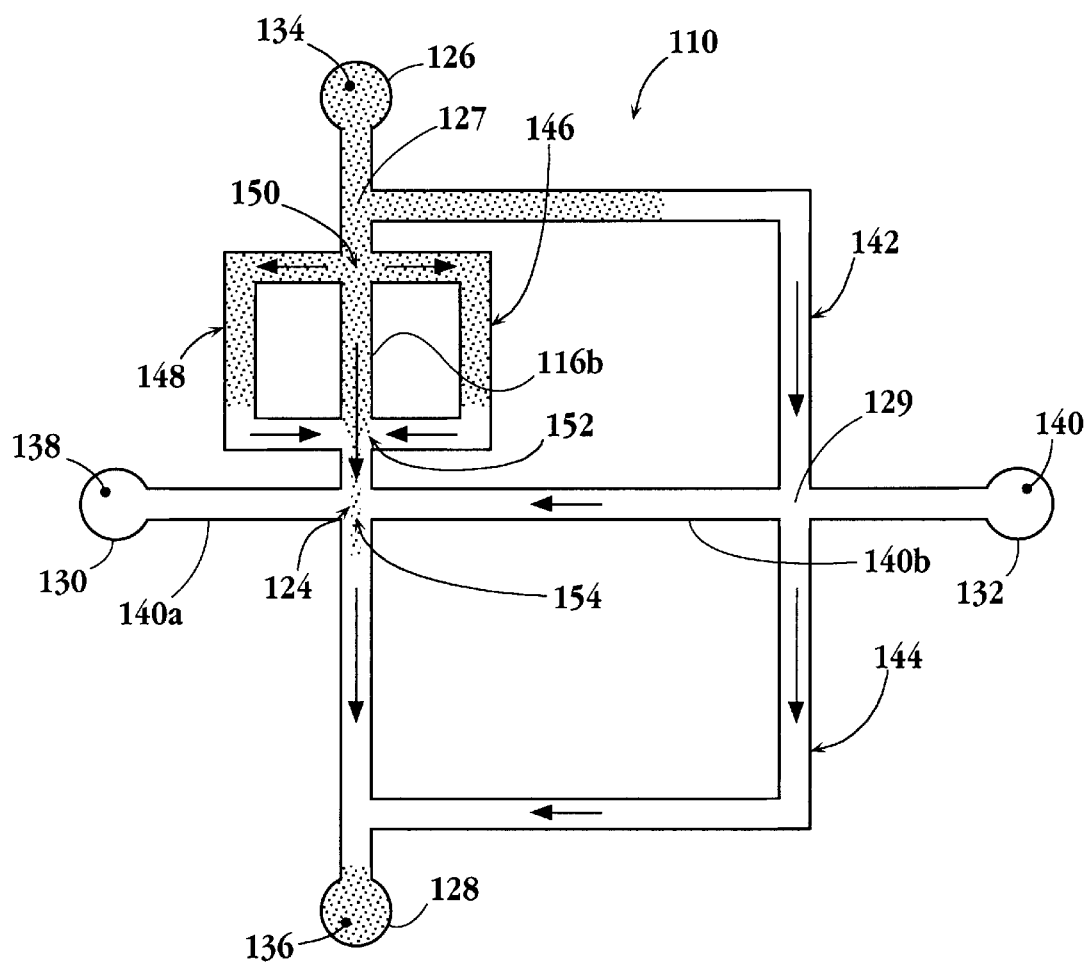
FIG. 14 is the same view of the device in FIG. 13, showing the formation of a sample volume with shaping at the intersection.

In FIG. 14 is depicted the next phase of the process, namely the loading of a shaped sample. It is understood, that in referring to streams, it may intend streams of ions as occurs in electrophoresis, liquid and ions as in electroosmosis or streams of liquid as in pneumatics. In performing the operation by electrophoresis, electrodes would be contacted with the liquid in the reservoirs 126, 128. Depending upon the nature of the ions, a voltage gradient would be created, where the ions would migrate from reservoir 126 toward reservoir 128. Since the electrical field would permeate all of the channels with varying field strengths, there would be ion migration through all of the channels. The extent of the migration in each channel will depend on the distance from the source, the length of the channel, the resistance to the migration of the ions in the channel and the strength of the field in the channel, as discussed above.

As depicted in FIG. 14, the sample indicated with shading migrates from the reservoir 126 to intersection 124 in the separation channel. This is driven by having electrodes 134, 136 activated, while allowing electrodes 138, 140 float. At the intersection 127, sample ions will proceed toward intersection 129 through second peripheral channel 142. Because of the longer pathway for migration of ions through peripheral channel 142 compared to the supply channel 116, the ions will move more slowly through this channel and will not be involved with the delivery and pinching process.

At intersection 150, the sample ions will divide between the three channels, the supply channel section 116b, and the two peripheral channels 146, 148. The resistance to flow of the ions in the supply channel section is less than in the proximal peripheral channels 146, 148. Therefore, the ions will migrate more rapidly down the supply channel past intersections 152, 154.

The field in the peripheral channels 146, 148, as well as the migration of the sample ions into these channels will move buffer ions into the intersection 152, confining the sample ions to a narrow stream 154, referred to as a shaped sample stream. The narrow sample stream will continue down the supply channel through the intersection 154 as a narrowly confined stream. There will be a slight flow in separation channel section 140b toward intersection 154 to further shape the sample stream. There will be little flow, if any from reservoir 130 toward intersection 152, since there will be substantially no field in separation channel section 140a, since electrode 138 is floating. The result is sample loading of a shaped sample stream through the sample-volume region within the separation channel.

In FIG. 15 the sample-injection phase of the process of delivery and separation is depicted. This figure depicts the situation after one has formed the shaped sample stream and the sample is injected at the intersection of the separation channel into the separation channel section 140b. At this stage, electrodes 134, 136 are allowed to float, while electrodes 138, 140 are activated, e.g., given a voltage potential to drive liquid and/or ions electrokinetically from reservoir 130 toward reservoir 132. As can be appreciated from the drawing, sample pullback into the sample and drain channels occurs by virtue of electrolyte movement toward reservoir 140 in peripheral channels 142, 144, as described above.

The separation channel section 140b may contain a sieving matrix to provide for separation of ions based on their mobility. Therefore, the different components of the sample will separate into different fractions 156, as shown. Usually a detector will be employed to detect the individual fractions when they move past a viewing position upstream of (to the right of) intersection 160 adjacent the downstream end of the separation channel.

Figure 17:
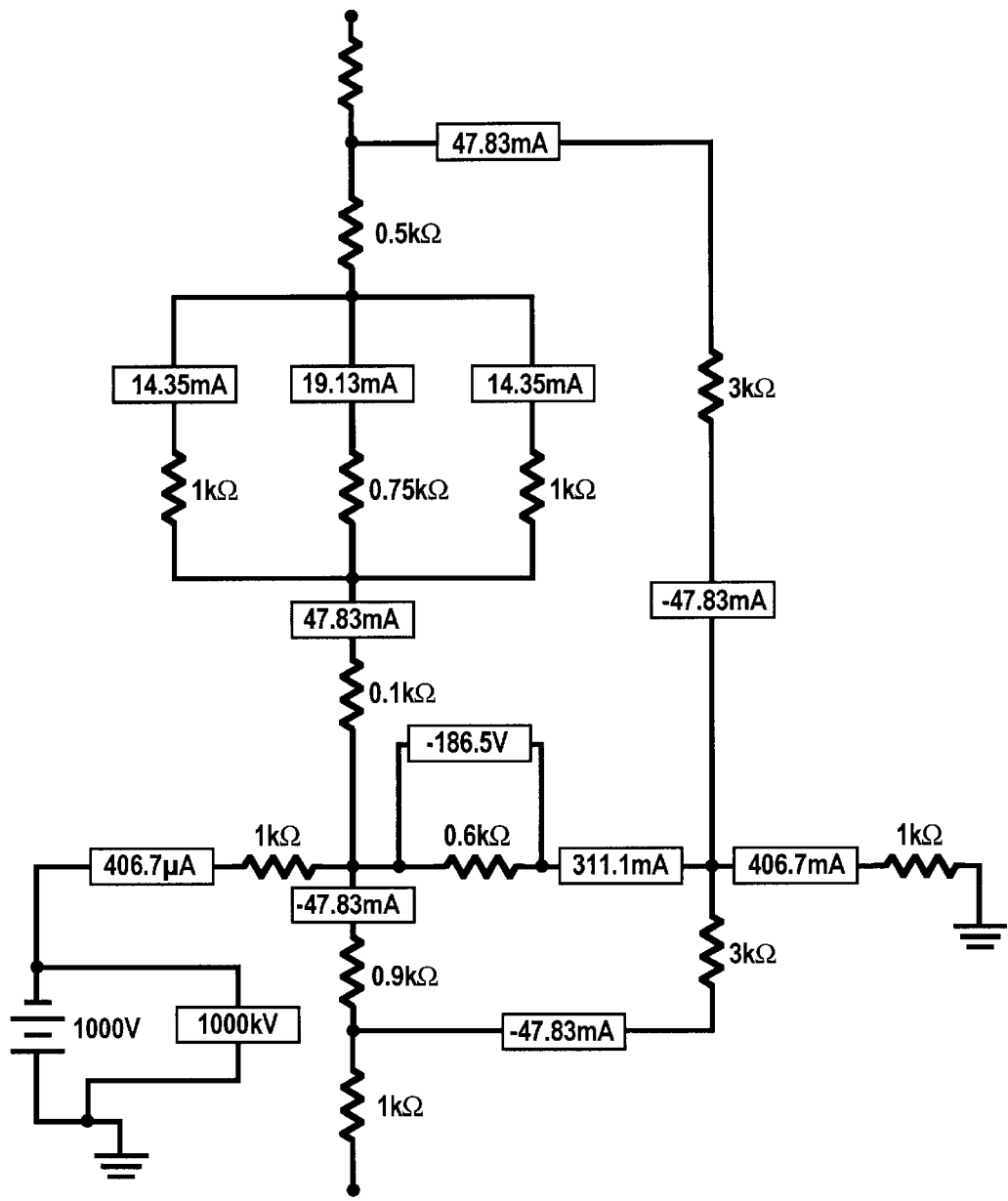

FIGS. 16 and 17 are electrical diagrams indicating exemplary resistances, applied voltages, and resulting currents in the device for performing sample delivery/pinch and injection/separation, respectively. It is to be understood that scaling applies, so that, for example, k may be increased to M and mA would be concurrently reduced to A. The diagrams conform to what is happening in FIGS. 14 and 15, respectively. The combinations of channel resistances and applied voltages can be altered to achieve other desired currents in each segment of the channel network.

It is evident from the above description that improved and simplified methods are provided for performing electrokinetic operations in a microfluidic card device. The operations use only a pair of electrodes at any one time and provide for accurate pinching and injection, with subsequent separation. By appropriate design of the device, pinching and pull back automatically occur in conjunction with a potential gradient created by two electrodes through the network of channels. Different configurations are possible within the context of the two-electrode operation. Various additional microstructures may be added for additional processes and operations in performing chemical or physical operations.

Furthermore, the microchannel networks having a buffer reservoir associated with the sample reservoir has a number of advantages in allowing for longer or multiple deliveries and injections without sample entering the separation channel from separation waste reservoir. The buffer reservoir also reduces the effect of conductivity changes in channels as the operation proceeds.

It is evident from the above description that improved and simplified methods are provided for performing electrokinetic operations in a microfluidic card device. The operations use only a pair of electrodes at any one time, meaning that only "one-channel" high voltage power supply is needed, and the operations provide for accurate pinching and injection, with subsequent separation. By appropriate design of the device, pinching and pull back automatically occur in conjunction with a potential gradient created by two electrodes through the network of channels. Different configurations are possible within the context of the two-electrode operation. Various additional microstructures may be added for additional processes and operations in performing chemical or physical operations.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An improved microfluidics device having a supply channel for holding a sample, a drain channel, and a separation channel for containing an electrolyte buffer, where said supply and drain channels intersect said separation channel at a supply port and a drain port, respectively, which ports define a sample-volume region in the separation channel between the two ports, and first, second, third, and fourth reservoirs communicating with the supply channel, the drain channel, and upstream and downstream ends of the separation channel, respectively, such that applying an electrokinetic or pneumatic force between the first and second reservoirs is effective to move a sample from the first reservoir through the sample-volume region in the separation channel and into the drain channel, and applying an electrokinetic or pneumatic force between the third and fourth reservoirs is effective to move a sample in the sample-volume region in the separation channel in a downstream direction, the improvement being an improvement for sample volume control, comprising at least one of the following channel configurations:

(a) first and second peripheral channels connecting the supply channel to upstream and downstream regions of the separation channel, respectively, on opposite sides of the sample-volume region, such that applying an electrokinetic or pneumatic force between the first and second reservoirs is effective to move a sample from the first reservoir through the supply channel, the sample-volume region in the separation channel and into the drain channel, via the supply and drain channels, and to move electrolyte solution contained in the first and second peripheral channels and upstream and downstream regions of the separation channel toward the sample-volume region and into the drain channel, thereby shaping the sample in the sample-volume region during sample loading; and (b) said second peripheral channel peripheral channel connecting the supply channel and the drain channel, respectively, to a downstream region of the separation channel, respectively, such that applying an electrokinetic or pneumatic force between the third and fourth reservoirs is effective to move a sample in the sample-volume region in the separation channel in a downstream direction, and to move electrolyte solution contained in the upstream region of the separation channel through the second and third peripheral channels, thereby moving sample contained in the supply and drain channels away from the sample-volume region of the separation channel during sample injection.

2. The improvement of claim 1, further comprising means for placing an electric voltage potential difference between the reservoirs, wherein the force applied between the reservoirs is an electrokinetic force.

3. The improvement of claim 1, which includes each of said first, second, and third peripheral channels, whereby said first and second peripheral channels are for shaping sample in the sample-volume region during sample loading, and said third peripheral channel, is for cooperating with the second peripheral channel during sample injection, to move sample contained in the supply and drain channels away from the sample-volume region of the of the separation channel.

4. The improvement of claim 3, further comprising means for placing an electric voltage potential difference between the reservoirs, wherein the force applied between the reservoirs is an electrokinetic force by.

5. The improvement of claim 3, which further includes a fourth peripheral channel connecting the drain channel to an upstream portion of the separation channel.

6. The improvement of claim 1, wherein the sample and drain ports are axially aligned within the separation channel, and the sample-volume region includes the region between the two ports.

7. The improvement of claim 1, wherein the sample and drain ports are longitudinally offset along the separation channel, and the sample-volume region includes the region of the separation channel between the two ports, including the ports themselves.

8. The improvement of claim 1, which includes said first and second peripheral channels, and which further includes a supply pair of peripheral channels, each of which extends from a first region point along the supply channel, adjacent the first reservoir, and a region along the supply channel adjacent the intersection of the supply channel with the separation channel, such that applying an electrokinetic or pneumatic force between the first and second reservoirs is effective to move a sample from the first reservoir through the supply channel toward the separation channel, and to move electrolyte solution contained in the supply pair of peripheral channels from the first to the second regions in the supply channel, thereby shaping the sample in the supply channel as it is moved into the sample-volume-region of the separation channel.

9. The improvement of claim 1, wherein at least one of the first and second peripheral channels is configured to have a higher resistance to fluid flow, when an electrokinetic or pneumatic force is applied between the first and second reservoirs, than the fluid flow resistance of the supply channel.

10. The improvement of claim 1, wherein at least one of the second and third peripheral channels is configured to have a higher resistance to fluid flow, when an electrokinetic or pneumatic force is applied between the third and fourth reservoirs, than the fluid flow resistance of the separation channel.

11. An improved microfluidics system for use in sample handling, comprising (a) the improved microfluidics device of any of claims 1–10, (b) electrodes adapted to contact liquid contained in the device reservoirs, and (c) a control unit for controlling the electric potential difference between the first and second reservoirs, during sample loading, and between the third and fourth and reservoirs, during sample injection.

* * * * *